United States Patent [19]

Hayden et al.

[11] Patent Number: 6,060,043
[45] Date of Patent: May 9, 2000

[54] DEODORANT COMPOSITION CONTAINING D-AMINO ACID

[75] Inventors: Patrick Joseph Hayden, Germantown; Virginia Streusand Goldman, Potomac, both of Md.

[73] Assignee: The Gillette Company, Boston, Mass.

[21] Appl. No.: 09/017,691

[22] Filed: Feb. 3, 1998

[51] Int. Cl.[7] ............................ A61K 7/32; A61K 7/34; A61K 7/38; A61K 7/00
[52] U.S. Cl. .............................. 424/65; 424/47; 424/66; 424/68; 424/400; 424/401; 424/DIG. 5
[58] Field of Search ............................. 424/65, 47, 66, 424/68, 400, 401, DIG. 5

[56] References Cited

U.S. PATENT DOCUMENTS

| | | | |
|---|---|---|---|
| 4,031,231 | 6/1977 | Kahan | 424/272 |
| 5,213,791 | 5/1993 | Lyon et al. | 424/65 |
| 5,595,728 | 1/1997 | Brocket et al. | 424/65 |

OTHER PUBLICATIONS

Manning, et al., Proc. Nat. Acad. Sci. USA, 71:417–421, (1974).

Patchett, A. A., et al., Soc. Chem. Ind. (Lond.) Monogr., 42:109–118, 1989.

*Primary Examiner*—Shelley A. Dodson
*Attorney, Agent, or Firm*—Stephan P. Williams; Laurence P. Hobbes

[57] ABSTRACT

A deodorant composition is disclosed which comprises a body odor suppressing effective amount of an optically active bactericide comprising D-amino acid, e.g., at least one selected from the group consisting of β-chloro-D-alanine and D-cycloserine, in a dermatologically acceptable carrier. A method is also provided for inhibiting body odor by applying to the skin a body odor suppressing effective amount of the bactericide.

20 Claims, No Drawings

DEODORANT COMPOSITION CONTAINING D-AMINO ACID

BACKGROUND OF THE INVENTION

1. Field of the Invention

This invention relates to inhibition of body odor, and more particularly to an optically active deodorant ingredient, deodorant composition containing said ingredient, and a method for inhibiting malodor formation by applying such composition.

2. Description of the Prior Art

As is well known, the mechanism of formation of the most common type of body odor is based upon the action of microorganisms on eccrine and apocrine sweat. Axillary bacteria act on the proteinaceous secretions present in sweat to produce the pungent odor known as axillary malodor. As a consequence of this mechanism there are in wide commercial use today in the over-the-counter toiletries and cosmetics category two types of products that inhibit body odor, deodorants and antiperspirants, the latter group also occasionally referred to as antiperspirant/deodorants. The former group is meant to include products containing an active material which inhibits the growth of microorganisms present on the skin and thereby prevent their action on sweat to produce odoriferous substances. The latter group is meant to include products which contain materials that inhibit sweating in the first place. For various reasons, such as aesthetic preference, sensitivity to certain astringent antiperspirant salts, etc., individual consumers who wish to use a product in this broad category may prefer one or the other type. The present invention is particularly concerned with improvements in deodorants.

Current deodorants are generally of two types: odor maskers and germicides. Despite the many disclosures in the art pertaining to deodorant compositions, current products are not sufficient to suppress odor in a significant proportion of the population, particularly during periods of "stress." Thus, there remains a need for deodorant compositions and methods which are effective, safe and economical.

It is well known that many deodorant products contain ingredients which inhibit the growth of axillary bacteria. However, not all "bacteristatic" or "bactericidal" compounds will necessarily produce good deodorant products for several reasons. First, although many strains and species of bacteria exist, only a very few specific strains colonize the surface of the skin in the axilla and are responsible for producing axillary malodor. Bacteristatic and bactericidal compounds exhibit a wide range of potencies against any particular given bacterial strain, for example, a particular compound may be highly potent against one strain but yet completely ineffective against another. Good antibacterial deodorant compounds must therefore be effective against the specific strains of axillary bacteria which cause malodor. Secondly, good antibacterial deodorant ingredients need to maintain their activity for the desired length of time in the axilla. This means they must be physically, chemically, arid biochemically compatible with the product formulation and the environmental conditions of the axilla, and they must be sufficiently adherent to the skin so they are not rinsed or rubbed off. Thirdly, the compound needs to be safe, that is, non-toxic to the body and non-irritating to the skin with daily application of amounts which effectively inhibit the growth of axillary bacteria. Again, not just any anti-bacterial compound will fulfill these requirements. Thus, discovering a good antibacterial deodorant ingredient that will be clinically safe and effective for controlling axial malodor is far from a trivial task. This can be attested to by the fact that among the many hundreds of known antibacterial compounds, there are relatively few that have been successfully used in deodorant products.

While known deodorants usually have good antimicrobial properties, it does not follow that good antimicrobials will be effective as deodorants. For example, the following antimicrobial materials were tested for deodorant activity, and no improvement over currently available materials was observed; in some cases no deodorant activity was observed at all: hydrogen peroxide, chlorhexidine, triacetin, and 3-(trimethoxysilyl)propyloctadecyldimethyl ammonium chloride (Dow-Corning, Q9-5700). Other workers have also noted this poor correlation between antimicrobial activity and deodorant activity; see, for example, Dravnieks, Krotoszynski, Lieb, and Jungermann, "Influence of an Antibacterial Soap on Various Effluents from Axillae," J.Soc. Cosmetic Chemists, 19, 611–626 (1968) and Cowen, "Relative Merits of 'In Use' and Laboratory Methods for the Evaluation of Antimicrobial Products, "J. Soc. Cosmetic Chemists, 25, 307–323 (1974).

The ability of certain D-amino acids to inhibit bacterial cell wall synthesis is disclosed by Manning, et al., Proc. Nat. Acad. Sci. USA, 71: 417–421, (1974). These compounds have been used as systemic antibiotic products: however, such use was abandoned due to systemic side effects as disclosed by Patchett, A. A., et al., Soc. Chem. Ind. (Lond.) Monogr., 42: 109–118, 1989, presumably due to metabolism of the compounds by D-amino acid oxidase present in the kidney. Topical use of these compounds as antibacterial or deodorant products was not taught.

Alanine analogues, e.g., D-cycloserine and $\beta$- chloro-D-alanine, among others, are known to exhibit antibiotic activity by inhibiting specific target enzymes, e.g., alanine racemase and D-alanine:D-alanine ligase, and D-amino acid transaminase. This interferes with the assembly of peptidoglycans, resulting in disruption of cell wall structure. See, Neuhaus, et al., Pharmac. Ther., Vol. 14, pp. 265 to 319. The reference also discloses in vitro synergistic antibacterial activity for a mixture of $\beta$-fluoro-D-alanine and D-cycloserine (id. at 304).

The use of beta-halo-,alpha-halo-, or alpha-methyl-alanines, or cycloserine as inhibitors of bacterial malodor-producing enzymes (pyridoxal phosphate- or PLP-dependent enzymes) in deodorant products is disclosed in U.S. Pat. No. 5,487,886 to Lyon, et al. However, no mention is made therein of bactericidal activity such as bacterial cell wall synthesis or growth inhibition. Indeed, the reference teaches that cycloserine's deodorant activity results from its beta-lyase enzyme inhibition activity and further teaches away from the bactericide of the present invention by disclosing that trifluoroalanine and L-cycloserine had no inhibitory effect on the growth of Staphylococcus cells in culture. Moreover, the reference is silent with respect to D-isomers and does not disclose or suggest the use of D-amino acids inasmuch as it is directed to a mechanism for suppressing body odor by inhibiting amino acid $\beta$-lyase enzyme using L-amino acids.

U.S. Pat. Nos. 5,213,791 and 5,595,728 disclose the testing of $\beta$-substituted amino acids such as $\beta$-chloroalanine as well as cycloserine for their activity against malodor-forming enzyme in the presence of whole cells.

Contrary to literature reports of studies using other bacterial strains, $\beta$-halo-L-alanines are not effective for inhibiting bacterial cell wall synthesis and bacterial cell growth of malodor-producing strains of axillary bacteria. $\beta$-halo-L- alanines also suffer from the disadvantage of inhibiting many other PLP-dependent enzymes in the skin and potentially other human tissues. For example, topical application of β-chloro-L-alanine irreversibly inhibits serine-palmitoyl transferase in the skin, and alters recovery of skin barrier function in vivo as noted by Holleran, W. M., et al., J. Clinic. Invest. 88: 1338–1345, 1991. Thus, use of β-halo-L-alanines suffers from a significant potential to cause skin irritation and other undesirable effects.

Accordingly, it would be desirable to provide a deodorant composition which exhibits effective deodorant activity without causing skin irritation or alteration of skin barrier function.

SUMMARY OF THE INVENTION

The present invention relates to a deodorant composition comprising a body odor suppressing effective amount of an optically active bactericide comprising D-amino acid, in a dermatologically acceptable carrier. In one aspect of the invention, the D-amino acid can be selected from the following groups of amino acids in the D-form:

Group 1: amino acids containing a halogen at the β-carbon with the formula $NH_2$—$CH(R)COOH$ where R is selected from the group consisting of i) —$CH_2ONH_2$ and ii) —$CR^1R^2R^3$ where $R^1$ is a halogen and $R^2$ and $R^3$ are the same or different and are selected from the group consisting of hydrogen, chlorine, fluorine, iodine, bromine, a phenyl group, and $C_1$–$C_8$ alkyl which is unsubstituted or substituted by a moiety selected from the group consisting of phenyl, hydroxy, carboxy, benzyloxy, benzyloxycarbonyl, halogen, and amino;

Group 2: α-Methyl amino acids of the formula $NH_2$—$C(CH_3)(COOH)$—R where R is selected from the group consisting of hydrogen, phenyl, and $C_1$–$C_8$ alkyl which is unsubstituted or substituted by a moiety selected from the group consisting of phenyl, hydroxy, carboxy, benzyloxy, benzyloxycarbonyl, halogen, and amino;

Group 3: Cycloserine and related cyclic amino acids of the formula:

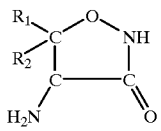

where $R^1$ and $R^2$ are selected from the group consisting of hydrogen, phenyl, and $C_1$–$C_8$ alkyl which is unsubstituted or substituted by a moiety selected from the group consisting of phenyl, hydroxy, carboxy, benzyloxy, benzyloxycarbonyl, halogen, and amino.

In another aspect of the present invention, the D-amino acid is selected from the group consisting of D-alanine, alpha-halogen-substituted D-alanine, beta-halogen-substituted D-alanine, alpha-alkyl-substituted D-alanine, aminoxy-D-alanine and D-cycloserine, wherein halogen is selected from the group consisting of F, Cl, Br, and I, preferably F or Cl, and alkyl is preferably $C_1$ to $C_{10}$ alkyl. In an especially preferred embodiment of the present invention, the D-amino acid is selected from the group consisting of β-chloro-D-alanine and D-cycloserine.

In an especially preferred embodiment, the optically active deodorant composition is substantially free of skin-irritating amino acids.

In another aspect, the present invention relates to a method for inhibiting body odor by applying to the skin a body odor suppressing effective amount of an optically active bactericide selected from the D-amino acids as noted above, especially bactericide consisting of an element selected from the group consisting of β-chloro-D-alanine and D-cycloserine, in a dermatologically acceptable carrier.

DETAILED DESCRIPTION OF THE INVENTION

The present invention provides novel compositions and a novel method of suppressing body odor by the topical application of a composition containing D-amino acid inhibitors of axillary bacterial growth. The D-amino acids employed are believed to inhibit the growth of axillary bacteria by interfering with the activity of bacterial pyridoxal phosphate- (PLP-) dependent enzymes involved in the synthesis of the bacterial cell wall. The use of D-amino acids produces effective axillary odor reduction and bacterial growth inhibition in vivo without causing skin irritation or toxicity which can occur when the corresponding L-amino acids inhibit PLP-dependent enzymes present in the skin or other cells of the human body. Accordingly, the deodorant ingredient of the present invention is optically active, i.e., capable of rotating the plane of plane-polarized light, or non-racemic. The optically active deodorant ingredient preferably can contain no more than 20% L-amino acids, preferably no more than 10% L-amino acids, e.g., 10% L-amino acids and 90% D-amino acids. More preferably, the deodorant ingredient of the present invention, or even the entire deodorant composition itself, is substantially free of the corresponding L-amino acids, i.e., consists essentially of the specified D-amino acids.

The D-amino acids employed in the present invention include commercially available D-amino acids, e.g., β-chloro-D-alanine and D-cycloserine which are commercially available from Sigma Chemical Company of Saint Louis, Mo.

The deodorant benefits of utilizing the D-amino acids of the present invention are suited to their use in a wide variety of products in the cosmetics and toiletries field. For example, the deodorant benefits of utilizing these D-amino acids may be realized by their incorporation in a carrier to provide a composition in the form of a solution, lotion, cream, ointment, powder, suspension, stick, gel, or aerosol. The carrier can comprise a vehicle selected from the group consisting of water, ethanol, polyhydric alcohol, silicone, fatty alcohol, fatty acid, fatty acid ester and mixtures thereof. The minimum effective concentration of the D-amino acid components can be determined by routine trial-and-error. At high concentrations cost considerations militate against using too much of the inhibitor. Amounts of D-amino acid component can range from 0.01 wt. % to 5 wt. %, preferably 0.05 wt. % to 2 wt. % of the total deodorant composition. The D-amino acid anti-bacterials described in this invention will be most stable at acidic to neutral pH.

The present invention is especially advantageous in that it can provide a deodorant composition which is essentially free of skin-irritating amino acids. By skin-irritating is meant amino acid compounds which are axilla skin irritating at levels of 1 wt. % or less.

The deodorant composition of the present invention can also include a germicide selected from the group consisting of triclosan, zinc phenol sulfonate and chlorhexidine digluconate in amounts ranging from 0.01 wt. % to 10 wt. %, preferably from 1 to 5 wt. % of the deodorant composition.

Although deodorancy is the most important concern for the consumer of underarm products, many also choose a product with antiperspirant activity. Current antiperspirants, which are aluminum salts, also function as deodorants by virtue of their germicidal properties. Thus, if desired, the deodorants of the present invention can be employed with the antiperspirant compounds well known in the art. In such formulations, the inhibitors of the malodor forming enzyme of the present invention can be incorporated into an antiperspirant formulation with the antiperspirant being employed in a perspiration reducing effective concentration.

The antiperspirant component used in the present invention may be any of those which contain aluminum, either alone or in combination with other materials such as zirconium. Typical aluminum salts, although not all-inclusive, include: Aluminum chlorohydrate; Aluminum sesquichlorohydrate; Aluminum dichlorohydrate; Aluminum chlorohydrex PG or PEG; Aluminum sesquichlorohydrex PG or PEG; Aluminum dichlorohydrex PG or PEG; Aluminum zirconium trichlorohydrate; Aluminum zirconium; Aluminum zirconium tetrachlorohydrate; Aluminum zirconium tetrachlorohydrex PG or PEG; Aluminum zirconium pentachlorohydrate; Aluminum zirconium octachlorohydrate; Aluminum zirconium trichlorohydrex-gly; Aluminum zirconium tetrachlorohydrex-gly; Aluminum zirconium pentachlorohydrex-gly; Aluminum zirconium octachlorohydrex-gly; Aluminum zirconium chloride; Aluminum zirconium sulfate; Potassium aluminum sulfate; Sodium aluminumchlorohydroxylacetate; and Aluminum bromohydrate.

In general, the active antiperspirant component should be present in the same amounts at which such materials are conventionally employed. As a rule, the antiperspirant composition should contain from 5 wt. % to 30 wt. %, preferably from 10 wt. % to 25 wt. % of the active antiperspirant salt component.

The invention may be further understood by reference to the following examples, but is not intended to be unduly limited thereby.

EXAMPLE 1

Effect of Bactericides β-chloro-D-alanine (BCA) and D-cycloserine on Axillary Bacteria Growth In Vitro In vitro experiments were conducted in order to determine the ability of several bacterial cell wall synthesis inhibitors to inhibit the growth of axillary bacteria. The minimum inhibitory concentrations (MIC) of β-chloro-D-alanine (BCA), and D-cycloserine were determined in Staphylococcus (*Staphylococcus haemolyticus*) and Coryneform strains of axillary bacteria as follows: Frozen stock cultures were thawed out and 50 µl of *Staphylococcus haemolyticus* or 100 µl of Coryneform bacteria were inoculated into 5.0 ml of nutrient media. Bacteria were incubated at 35° C. overnight to produce cultures in log phase growth. A series of tubes was set up into which serial dilutions of BCA or triclosan in nutrient media were added in the range of 0.1 to 0.0001 wt/v % (where 1 g/100 ml=1 wt/v %). The tubes were inoculated with 50 µl of log phase *Staphylococcus haemolyticus* or Coryneform cultures and incubated at 35° C. overnight. The MIC is defined as the lowest concentration of inhibitor in which the solutions did not become turbid due to bacterial growth. The minimum bactericidal concentration (MBC) was determined by adding 50 µl from each clear solution of the MIC experiment into 5.0 ml of fresh nutrient media and incubating overnight at 37° C. The MBC is defined as the lowest concentration of inhibitor in which the subcultures did not become turbid due to bacterial growth. The MIC of BCA was thus determined to be 0.1 wt/v % and 0.001 wt/v % in *Staphylococcus haemolyticus* and Coryneforms, respectively. The MIC of D-cycloserine was thus determined to be 0.01 wt/v % and 0.005 wt/v % in *Staphylococcus haemolyticus* and Coryneforms, respectively. By comparison, the MIC of the common antibacterial deodorant compound triclosan is 0.01 wt/v % and 0.1 wt/v % in *Staphylococcus haemolyticus* and Coryneforms, respectively.

EXAMPLE 2

BCA's Lack of In Vitro Inhibition of Bacterial Beta-Lyase in Whole Bacteria Cells BCA was tested for its ability to prevent *Staphylococcus haemolyticus* from metabolizing sweat to form malodor. Log-phase cultures of *Staphylococcus haemolyticus* were incubated with various concentrations of BCA (31–0.625 mM) in phosphate buffer (pH 6.8) for 30 minutes at 35° C. The cell/BCA mixture was then added to a "sniff vial" containing malodor precursors and incubated at 35° C. for an additional 30 minutes. Malodor compounds were then extracted from the mixture with chloroform and malodor was judged by spotting 10 µl of chloroform extracts onto bibulous paper and smelling. The results show that BCA did not inhibit malodor formed by staphylococcal metabolism of precursors. In contrast, the β-lyase inhibitor aminooxyacetic acid (AOA) consistently prevents malodor in the above assay at concentrations of 5.0 mM. The present results show that the D-amino acid BCA does not inhibit β-lyase when incubated with *Staphylococcus haemolyticus*.

U.S. Pat. Nos. 5,213,791 and 5,595,728 disclose the use of β-chloroalanine or cycloserine as deodorant actives by virtue of their ability to inhibit malodor production from bacterial malodor-forming enzyme (MFE) without killing or inhibiting the growth of the bacteria. These references disclose in vitro methodology for use in determining this form of activity. The methods involve incubating the potential inhibitor with live bacterial cells, bacterial cell homogenates or purified MFE in the presence of malodor precursors, and testing for the production of malodor. When both the D- and L- isomers of β-chloroalanine and cycloserine were tested by these methods, it was found that while the L-isomers were effective as a result of their β-lyase inhibitor activity, the D-isomers had virtually no effect for suppressing the production of malodor by live bacterial cells or purified MFE. This is significant because, according to the test methods and teachings of these references, the D-isomers of β-chloroalanine or cycloserine are predicted to be devoid of deodorant activity. The finding that D-amino acid derivatives are actually better deodorants as a result of bactericidal activity than the L-amino acid β-lyase inhibitors is unexpected or surprising in light of the prior art.

EXAMPLE 3

In Vivo Test for Axillary Irritation of 1.0% BCA

In vivo experiments were conducted to determine if 1.0% solutions of BCA were irritating to axillary skin. BCA was dissolved in a mixture of 60% propylene glycol and 40% water at a final concentration of 1.0%. The pH of the solution was adjusted to about 6.25 with 10 N NaOH. Seven panelists applied 1.0 ml of this test solution to a cotton applicator swab and applied the solution to either the right or left axilla. 1.0 ml of a control solution of 60% propylene glycol and 40% water was similarly applied to the other axilla. The side of application of the test or control solutions was assigned in a random fashion. This procedure was performed on four consecutive days. Axilla were monitored by a nurse for signs of skin irritation. No incidences of irritation were reported.

EXAMPLE 4

Inhibition of Axillary Bacteria Growth and Malodor by BCA Applied in Effective Amounts to the Underarm in a Suitable Vehicle BCA was dissolved in a mixture of 60% propylene glycol and 40% water at a final concentration of 1.0%. The pH of the solution was adjusted to about 6.25 with 10 N NaOH. Thirty-nine female panelists applied 0.5 ml of this test solution to either the right or left axilla and 0.5 ml of a comparative solution of 60% propylene glycol and 40% water to the other. The side of application of the test or comparative solutions was assigned in a random fashion. Twenty-four hours after application, each side of the panelists' axilla was judged for odor by a panel of trained odor judges on a scale of 0 (no odor) to 10 (very intense, disagreeable odor). This procedure was performed on four consecutive days. No incidences of irritation were reported. Analysis of the clinical results is summarized below:

Deodorant Efficacy

The BCA-containing product was significantly more effective than the 60% propylene glycol and 40% water comparative product, at the 95% confidence level, for measurements 3, 4 and composite.

Tables 1 and 2 below provide further results. Significance was measured in a two-tailed T-test al 95% confidence level and n=number of subjects.

TABLE 1

Malodor Evaluation

|  | A(Comparative Product) | B (BCA Product) |
|---|---|---|
| Control | 4.58 | 4.59 |
| 1 | 4.06 | 4.18 |
| 2 | 3.8 | 3.6 |
| 3 | 3.79 | 3.3 |
| 4 | 4.1 | 3.49 |

TABLE 2

Malodor Evaluation Results 24 hours drop from untreated Control

| Post-Appln Measurement | n | A (Compa-r-ative) | n | B (BCA) | n | A–B | signifi-cance |
|---|---|---|---|---|---|---|---|
| 1 | 36 | 0.52 | 36 | 0.41 | 33 | 0.11 | |
| 2 | 36 | 0.78 | 36 | 0.99 | 33 | −0.21 | |
| 3 | 38 | 0.79 | 38 | 1.29 | 33 | −0.50 | * |
| 4 | 34 | 0.48 | 34 | 1.10 | 33 | −0.62 | ** |
| com-posite | 33 | 0.67 | 33 | 0.96 | 33 | −0.29 | * |

\* = significant at the 95% confidence level
\*\* = significant at the 99% confidence level

EXAMPLE 5

In Vivo Comparison of D-Cycloserine with Triclosan

A test product containing 1.0% D-cycloserine in 60% propylene glycol/40% water was compared to a product containing 0.3% triclosan in 60% propylene glycol/40% water by application to 60 test subjects according to the procedure of Example 4. The results were obtained by odor judges and are presented below in Table 3. The odor judge results indicated that the 1.0% D-cycloserine product was superior to 0.3% triclosan for inhibiting axillary malodor on all and the composite. All differences were highly significant.

TABLE 3

Judges' Malodor Evaluation Results

| | Post-Application Measurement | | 24 Hour Drop from Control | | |
|---|---|---|---|---|---|
| Day | D-cSer | Triclosan | D-cSer (drop) | Triclosan (drop) | Significance |
| Control | 4.7 | 4.72 | | | |
| 1 | 3.64 | 4 | 1.1 | 0.67 | * |
| 2 | 3.75 | 4.26 | 0.99 | 0.46 | * |
| 3 | 3.53 | 3.97 | 1.22 | 0.74 | * |
| 4 | 3.52 | 4 | 1.22 | 0.72 | * |
| Composite | 3.61 | 4.07 | 1.13 | 0.65 | * |

\* = significant at the 95% confidence level

EXAMPLE 6

In Vivo Comparison of β-chloro-D-alanine (BCA) with β-chloro-L-alanine

A test product containing 1.0% β-chloro-D-alanine (BCA)-cycloserine in 60% propylene glycol/40% water was compared to a comparative product containing 1.0% β-chloro-L-alanine in 60% propylene glycol/40% water by application to 50 female test subjects according to the procedure of Example 4. The results were obtained by odor judges and are presented below in Table 4. The odor judge results indicated, with the exception of the first post-application measurement, that the BCA test product was significantly more effective in controlling malodor than the comparative product for the remaining post-application measurements and the composite at the 95% level of confidence.

TABLE 4

Judges' Malodor Evaluation Results

| | Measurement | | 24 Hour Drop from Control | | |
|---|---|---|---|---|---|
| Post-Application | D-BCA (A) | L-BCA (B) | A–B (drop) | number of subjects (n) | Significance |
| 1 | 1.079 | 0.913 | 0.166 | 48 | |
| 2 | 1.492 | 1.040 | 0.452 | 50 | * |
| 3 | 1.678 | 1.013 | 0.665 | 50 | * |
| 4 | 1.862 | 1.333 | 0.529 | 45 | * |
| Composite | 1.519 | 1.083 | 0.436 | 44 | * |

\*Significant at 95% Confidence Level

There are of course, many alternate embodiments and modifications of the invention which are intended to be included within the scope of the following claims.

What is claimed is:

1. A deodorant composition comprising a body odor suppressing effective amount of an optically active bactericide comprising D-amino acid in a dermatologically acceptable carrier.

2. The composition of claim 1 wherein said D-amino acid is selected from the following groups of amino acids in the D-form:

Group 1: Amino acids containing a halogen at the β-carbon with the formula $NH_2$—$CH(R)COOH$ where R is selected from the group consisting of i) —$CH_2ONH_2$ and ii) —$CR^1R^2R^3$ where $R^1$ is a halogen and $R^2$ and $R^3$ are the same or different and are selected from the group consisting of hydrogen, chlorine, fluorine, iodine, bromine, a phenyl group, and $C_1$–$C_8$ alkyl which is unsubstituted or substituted by a moiety selected from the group consisting of phenyl, hydroxy, carboxy, benzyloxy, benzyloxycarbonyl, halogen, and amino;

Group 2: α-Methyl amino acids of the formula $NH_2$—$C(CH_3)(COOH)$—$R$ where R is selected from the group consisting of hydrogen, phenyl, and $C_1$–$C_8$ alkyl which is unsubstituted or substituted by a moiety selected from the group consisting of phenyl, hydroxy, carboxy, benzyloxy, benzyloxycarbonyl, halogen, and amino; and Group 3: Cycloserine and related cyclic amino acids of the formula:

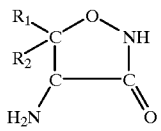

where $R^1$ and $R^2$ are selected from the group consisting of hydrogen, phenyl, and $C_1$–$C_8$ alkyl which is unsubstituted or substituted by a moiety selected from the group consisting of phenyl, hydroxy, carboxy, benzyloxy, benzyloxycarbonyl, halogen, and amino.

3. The composition of claim 1 wherein said D-amino acid is selected from the group consisting of D-alanine, alpha-halogen-substituted D-alanine, beta-halogen-substituted D-alanine, alpha-alkyl-substituted D-alanine, aminoxy-D-alanine, and D-cycloserine.

4. The composition of claim 1 wherein said D-amino acid is β-chloro-D-alanine.

5. The composition of claim 1 wherein said D-amino acid is D-cycloserine.

6. The composition of any one of claims 1, 4, or 5 which further comprises an antiperspirant salt.

7. The composition of any one of claims 1, 4, or 5 wherein said bactericide is present in an amount of from 0.01 wt. % to 5 wt. %.

8. The composition of any one of claims 1, 4, or 5 wherein said bactericide is present in an amount of from 0.05 wt. % to 2 wt. %.

9. The composition of claim 1 in the form of a solution, lotion, cream, ointment, powder, suspension, stick, gel, or aerosol.

10. The composition of claim 1 wherein said carrier comprises a vehicle selected from the group consisting of water, ethanol, polyhydric alcohol, silicone, fatty alcohol, fatty acid, fatty acid ester and mixtures thereof.

11. The composition of any one of claims 1, 4, or 5 wherein said deodorant composition further comprises a germicide selected from the group consisting of triclosan, zinc phenol sulfonate and chlorhexidine digluconate.

12. The composition of any one of claims 1, 4, or 5 which is substantially free of L-amino acids.

13. A method for inhibiting body odor by applying to the skin a body odor suppressing effective amount of an optically active bactericide comprising D-amino acid in a dermatologically acceptable carrier.

14. The method of claim 13 wherein said D-amino acid is selected from the following groups of amino acids in the D-form:

Group 1: Amino acids containing a halogen at the β-carbon with the formula $NH_2$—$CH(R)COOH$ where R is selected from the group consisting of i) —$CH_2ONH_2$ and ii) —$CR^1R^2R^3$ where $R^1$ is a halogen and $R^2$ and $R^3$ are the same or different and are selected from the group consisting of hydrogen, chlorine, fluorine, iodine, bromine, a phenyl group, and $C_1$–$C_8$ alkyl which is unsubstituted or substituted by a moiety selected from the group consisting of phenyl, hydroxy, carboxy, benzyloxy, benzyloxycarbonyl, halogen, and amino;

Group 2: α-Methyl amino acids of the formula $NH_2$—$C(CH_3)(COOH)$—$R$ where R is selected from the group consisting of hydrogen, phenyl, and $C_1$–$C_8$ alkyl which is unsubstituted or substituted by a moiety selected from the group consisting of phenyl, hydroxy, carboxy, benzyloxy, benzyloxycarbonyl, halogen, and amino; and Group 3: Cycloserine and related cyclic amino acids of the formula:

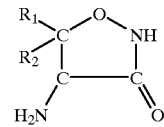

where $R^1$ and $R^2$ are selected from the group consisting of hydrogen, phenyl, and $C_1$–$C_8$ alkyl which is unsubstituted or substituted by a moiety selected from the group consisting of phenyl, hydroxy, carboxy, benzyloxy, benzyloxycarbonyl, halogen, and amino.

15. The method of claim 13 wherein said D-amino acid wherein said D-amino acid is selected from the group consisting of D-alanine, alpha-halogen-substituted D-alanine, beta-halogen-substituted D-alanine, alpha-alkyl-substituted D-alanine, aminoxy-D-alanine, and D-cycloserine.

16. The method of claim 13 wherein said bactericide comprises D-amino acid selected from the group consisting of β-chloro-D-alanine and D-cycloserine.

17. The method of claim 13 or 16 wherein said optically active bactericide contains no more than 20% L-amino acids.

18. The method of claim 13 or 16 wherein said bactericide is substantially free of L-amino acids.

19. The method of claim 13 or 16 wherein said carrier further comprises an antiperspirant salt.

20. The method of claim 13 or 16 wherein said bactericide is present in an amount of from 0.01 wt. % to 5 wt. % of said carrier.

* * * * *